(12) United States Patent
de Cogan

(10) Patent No.: US 10,526,691 B2
(45) Date of Patent: Jan. 7, 2020

(54) FUNCTIONALIZED SURFACE

(71) Applicant: The University of Birmingham, Birmingham (GB)

(72) Inventor: Felicity Jane de Cogan, Birmingham (GB)

(73) Assignee: The University of Birmingham, Birmingham (GB)

(*) Notice: Subject to any disclaimer, the term of this patent is extended or adjusted under 35 U.S.C. 154(b) by 0 days.

(21) Appl. No.: 15/741,194

(22) PCT Filed: Jul. 11, 2016

(86) PCT No.: PCT/GB2016/052080
§ 371 (c)(1),
(2) Date: Dec. 29, 2017

(87) PCT Pub. No.: WO2017/006139
PCT Pub. Date: Jan. 12, 2017

(65) Prior Publication Data
US 2019/0055639 A1 Feb. 21, 2019

(30) Foreign Application Priority Data

Jul. 9, 2015 (GB) .................................. 1512031.4

(51) Int. Cl.
| | | |
|---|---|---|
| *C23C 8/80* | (2006.01) | |
| *A01N 37/46* | (2006.01) | |
| *A01N 25/34* | (2006.01) | |
| *A01N 25/08* | (2006.01) | |
| *B05D 1/18* | (2006.01) | |
| *B05D 7/14* | (2006.01) | |
| *B05D 7/24* | (2006.01) | |
| *C23C 8/26* | (2006.01) | |
| *C23C 8/54* | (2006.01) | |

(52) U.S. Cl.
CPC ............... *C23C 8/80* (2013.01); *A01N 25/08* (2013.01); *A01N 25/34* (2013.01); *A01N 37/46* (2013.01); *B05D 1/18* (2013.01); *B05D 7/14* (2013.01); *B05D 7/24* (2013.01); *C23C 8/26* (2013.01); *C23C 8/54* (2013.01); *B05D 2202/15* (2013.01); *B05D 2202/35* (2013.01)

(58) Field of Classification Search
CPC ........ A01N 25/08; A01N 25/34; A01N 37/46; B05D 1/18; B05D 2202/15; B05D 2202/35; B05D 7/14; B05D 7/24; C23C 8/26; C23C 8/54; C23C 8/80
See application file for complete search history.

(56) References Cited

U.S. PATENT DOCUMENTS 6,613,432 B2 * 9/2003 Zamora .................. A61L 29/08
427/2.24
2017/0057998 A1 * 3/2017 Stamboulis ............. A61L 27/54

FOREIGN PATENT DOCUMENTS

| EP | 1295615 A1 | 3/2003 |
| EP | 1574132 A2 | 9/2005 |
| JP | 2010184022 A | 8/2010 |
| WO | 01/45862 A1 | 6/2001 |
| WO | 2013/076666 A1 | 5/2013 |
| WO | 2013/183048 A1 | 12/2013 |
| WO | 2015/128643 A1 | 9/2015 |

OTHER PUBLICATIONS

Cavalcanti, I. M. G., et al, "Salivary pellicle composition and multispecies biofilm developed on titanium nitrided by cold plasma", Archive of Oral Biology. 59 (2014), 695-703.
Dong, Y., et al, "Towards long-lasting antibacterial stainless steel surfaces by combining double glow plasma silvering with active screen plasma nitriding", Acta Biomaterialia, 7 (2011), 447-457.
Masao Yoshinari, et al, "Prevention of biofilm formation on titanium surfaces modified with conjugated molecules comprised of antimicrobial and titanium-binding peptides", BIOFOULING, vol. 26, No. 1, Oct. 16, 2009, pp. 103-110.
Goulter Rebecca M, et al, "*Escherichia coli* strains expressing H12 antigens demonstrate an increased ability to attach to abiotic surfaces as compared with *E. coli* strains expressing H7 antigens", Colloids and Surfaces. B, Biointerfaces, vol. 119, May 14, 2014, pp. 90-98.
Hisako Saido-Sakanaka, et al, "In vitro and in vivo activity of antimicrobial peptides synthesized based on the insect defensin", Peptides. vol. 25, No. 1, Jan. 1, 2004, pp. 19-27.
British Search Report dated Jan. 16, 2017 issued in connection with British Patent Application No. GB1612012.3.
PCT Search Report and Written Opinion dated Oct. 24, 2016 issued in connection with PCT Application No. PCT/GB2016/052080.

* cited by examiner

*Primary Examiner* — Marcela M Cordero Garcia
(74) *Attorney, Agent, or Firm* — Brooks Kushman P.C.

(57) ABSTRACT

Provided is a nitrided metal surface functionalized with molecules, each molecule comprising at least one binding group and an antimicrobial moiety. The molecules are immobilized on the surface by only covalent interactions between the binding groups of the molecules and nitrogen atoms within the nitrided metal surface. Articles comprising the functionalized nitrided surface find use in inhibiting or reducing the growth of microorganisms on surfaces that are frequently touched. A method for preparing the functionalized nitrided surface comprises contacting a nitrided metal surface with molecules so as to form covalent bonds between the binding groups of the molecules and the nitrogen atoms in the surface, thereby immobilising the molecules on the metal surface.

17 Claims, 13 Drawing Sheets
Specification includes a Sequence Listing.

A

B

SEQUENCE LISTING

```
<160> NUMBER OF SEQ ID NOS: 14

<210> SEQ ID NO 1
<211> LENGTH: 11
<212> TYPE: PRT
<213> ORGANISM: Artificial Sequence
<220> FEATURE:
<223> OTHER INFORMATION: Synthesized sequence

<400> SEQUENCE: 1

Arg Arg Tyr Ile Gly Arg Gly Tyr Ile Arg Arg
```

```
1               5                   10
```

<210> SEQ ID NO 2
<211> LENGTH: 9
<212> TYPE: PRT
<213> ORGANISM: Artificial Sequence
<220> FEATURE:
<223> OTHER INFORMATION: Synthesized sequence

<400> SEQUENCE: 2

```
Arg Leu Tyr Leu Arg Ile Gly Arg Arg
1               5
```

<210> SEQ ID NO 3
<211> LENGTH: 9
<212> TYPE: PRT
<213> ORGANISM: Artificial Sequence
<220> FEATURE:
<223> OTHER INFORMATION: Synthesized sequence

<400> SEQUENCE: 3

```
Cys Arg Val Arg Gly Gly Arg Cys Ala
1               5
```

<210> SEQ ID NO 4
<211> LENGTH: 6
<212> TYPE: PRT
<213> ORGANISM: Artificial Sequence
<220> FEATURE:
<223> OTHER INFORMATION: Synthesized sequence

<400> SEQUENCE: 4

```
Arg Arg Arg Arg Arg Arg
1               5
```

<210> SEQ ID NO 5
<211> LENGTH: 22
<212> TYPE: PRT
<213> ORGANISM: Artificial Sequence
<220> FEATURE:
<223> OTHER INFORMATION: Synthesized sequence

<400> SEQUENCE: 5

```
Arg Arg Arg Arg Arg Arg Gly Ala Leu Ala Gly Arg Arg Arg Arg
1               5                   10                  15

Arg Gly Ala Leu Ala Gly
            20
```

<210> SEQ ID NO 6
<211> LENGTH: 23
<212> TYPE: PRT
<213> ORGANISM: Artificial Sequence
<220> FEATURE:
<223> OTHER INFORMATION: Synthesized sequence

<400> SEQUENCE: 6

```
Gly Arg Arg Arg Arg Arg Arg Gly Ala Leu Ala Gly Arg Arg Arg
1               5                   10                  15

Arg Arg Gly Ala Leu Ala Gly
            20
```

<210> SEQ ID NO 7
<211> LENGTH: 22
<212> TYPE: PRT
<213> ORGANISM: Artificial Sequence
<220> FEATURE:

<223> OTHER INFORMATION: Synthesized sequence

<400> SEQUENCE: 7

Lys Lys Lys Lys Lys Lys Gly Ala Leu Ala Gly Lys Lys Lys Lys
1               5                   10                  15
Lys Gly Ala Leu Ala Gly
            20

<210> SEQ ID NO 8
<211> LENGTH: 11
<212> TYPE: PRT
<213> ORGANISM: Artificial Sequence
<220> FEATURE:
<223> OTHER INFORMATION: Synthesized sequence

<400> SEQUENCE: 8

Cys Arg Leu Tyr Leu Arg Ile Gly Arg Arg Cys
1               5                   10

<210> SEQ ID NO 9
<211> LENGTH: 24
<212> TYPE: PRT
<213> ORGANISM: Artificial Sequence
<220> FEATURE:
<223> OTHER INFORMATION: Synthesized sequence

<400> SEQUENCE: 9

Cys Arg Arg Arg Arg Arg Arg Gly Ala Leu Ala Gly Arg Arg Arg
1               5                   10                  15
Arg Arg Arg Gly Ala Leu Ala Gly Cys
            20

<210> SEQ ID NO 10
<211> LENGTH: 25
<212> TYPE: PRT
<213> ORGANISM: Artificial Sequence
<220> FEATURE:
<223> OTHER INFORMATION: Synthesized sequence

<400> SEQUENCE: 10

Cys Gly Arg Arg Arg Arg Arg Arg Gly Ala Leu Ala Gly Arg Arg
1               5                   10                  15
Arg Arg Arg Gly Ala Leu Ala Gly Cys
            20                  25

<210> SEQ ID NO 11
<211> LENGTH: 10
<212> TYPE: PRT
<213> ORGANISM: Artificial Sequence
<220> FEATURE:
<223> OTHER INFORMATION: Synthesized sequence

<400> SEQUENCE: 11

Cys Arg Val Arg Gly Gly Arg Cys Ala Cys
1               5                   10

<210> SEQ ID NO 12
<211> LENGTH: 8
<212> TYPE: PRT
<213> ORGANISM: Artificial Sequence
<220> FEATURE:
<223> OTHER INFORMATION: Synthesized sequence

```
<400> SEQUENCE: 12

Cys Arg Arg Arg Arg Arg Cys
1               5

<210> SEQ ID NO 13
<211> LENGTH: 24
<212> TYPE: PRT
<213> ORGANISM: Artificial Sequence
<220> FEATURE:
<223> OTHER INFORMATION: Synthesized sequence

<400> SEQUENCE: 13

Cys Lys Lys Lys Lys Lys Gly Ala Leu Ala Gly Lys Lys Lys Lys
1               5                   10                  15

Lys Lys Gly Ala Leu Ala Gly Cys
            20

<210> SEQ ID NO 14
<211> LENGTH: 13
<212> TYPE: PRT
<213> ORGANISM: Artificial Sequence
<220> FEATURE:
<223> OTHER INFORMATION: Synthesized sequence

<400> SEQUENCE: 14

Cys Arg Arg Tyr Ile Gly Arg Gly Tyr Ile Arg Arg Cys
1               5                   10
```

FUNCTIONALIZED SURFACE

REFERENCE TO SEQUENCE LISTING

A Sequence Listing is submitted herewith through EFS-Web as an ASCII compliant text file. The text file is named "7492135_ST25.txt", was created on Apr. 20, 2018, and is 3.67 kilobytes in size. The Sequence Listing is incorporated by reference herein.

The present invention relates to a functionalized surface, in particular a metal surface having molecules, including peptides, immobilized thereon by only covalent interactions.

Around one in every eleven patients acquires a nosocomial infection whilst in an NHS hospital at any given time. This costs the NHS hundreds of millions of pounds each year. Subsequently, reducing the spread of nosocomial infection is a key priority for the NHS.

Microbes have been shown to contaminate a multitude of surfaces, including, but not limited to, door handles, telephones, keyboards, taps, plastics and fabrics, such as scrubs and aprons. Further, it has been shown that 65% of nurses in direct contact with patients suffering from methicillin-resistant *Staphylococcus aureus* (MRSA) had contaminated clothing. An additional 42% of staff that had not been in direct contact with the infected patients, but had been in contact with surfaces in the hospital, also had contaminated clothing. This demonstrates that it is not only transmission between people that can enable a spread of infection, but also inanimate objects.

Following colonisation of a surface, a number of microbes have been shown to survive for a considerable amount of time. Some strains of MRSA have been seen to survive for up to 9 weeks after drying and parainfluenza virus has been shown to last up to 10 hours on a non-absorptive surface and 4 hours on an absorptive surface. These relatively long survival rates heighten the transmission capacity of the microbes in question by increasing the period of time in which they can infect other patients.

Despite the implementation of a hand washing protocol in UK hospitals, infection has still been able to spread. This may be due to varying compliance with the protocol itself or impracticality in the procedure, since staff come in to contact with a number of surfaces before they are able to reach a sink and wash their hands. This allows the contamination of surfaces from both staff and patients, enabling only a short period of relief from contamination for those who do wash their hands before they are re-infected. In addition, clothing can also become contaminated, providing an alternate route for the spread of microbes.

Although the cleaning of surfaces has been shown to decrease the spread of infection, it does not prevent re-colonization. Moreover, the initial cleaning process does not eradicate all microbes. For example, MRSA is known to persist following cleaning. In addition, visible cleanliness does not necessarily correlate with the level of microbial contamination, making it difficult to assess if a surface has been cleaned correctly without doing further microbial tests. No standard for acceptable surface microbial load has been agreed and the infectious dose varies greatly between patients and studies making it difficult to assess how much and when cleaning must take place.

It is apparent that surfaces play an important role in the passage of infectious agents between individuals. Current cleaning processes are temporary and inefficient; improved long-term antimicrobial control is required. Not only is the spread of infectious agents important in a healthcare setting, but also in many other environments, including public buildings, business premises, domestic dwellings, public transport, farms and areas associated with food preparation.

There is a clear need for an improved mechanism for the antimicrobial control of the environment, particularly surfaces.

The present invention has been devised with these issues in mind.

According to a first aspect of the present invention there is provided a nitrided metal surface functionalized with molecules, each molecule comprising at least one binding group and an antimicrobial moiety, wherein all of the molecules are immobilized on the surface by only covalent interactions between the binding groups of the molecules and nitrogen atoms within the nitrided metal surface.

The use of covalent interactions to immobilize molecules on a metal surface is advantageous since covalent interactions strongly bind the molecules to the surface, thereby preventing or reducing their release.

It will be appreciated that the binding group will comprise or consist of a functional group that is capable of forming a covalent bond with a nitrogen atom within the metal surface. The functional group may be, but is not necessarily limited to, a carboxyl group, an amine, an imine, a thioamide or an enamine. In some embodiments, the binding group comprises or consists of a carboxyl group. It will be appreciated that in such embodiments, the covalent interaction is an amide bond formed between the carboxyl group of each molecule and a nitrogen atom of the metal surface.

Thus, the use of a nitrided metal surface enables the molecules to be bound directly to the metal surface, without the need for linkers or additional functionalization of the metal surface.

The nitrided metal surface may be functionalized with a plurality of molecules.

While researchers have previously been able to bind molecules to metal surfaces using covalent interactions, this has relied upon coating the metal with a polymer or resin and then attaching the molecule to the coating. However, coating the surface of the metal with a polymer gives very different material properties to the metal, and also presents a much less durable material on the surface.

In addition to enabling direct bonding to the molecules via covalent linkages, the use of a nitrided metal surface is advantageous since the nitrogen present in the surface increases the wear resistance of the metal.

The attachment of molecules to surfaces to impart functionality is also desirable in fields such as detection, for example, contamination detection or environmental monitoring.

The molecules may be any molecule having antimicrobial activity. The molecule or the antimicrobial moiety thereof may have antibacterial, antiviral and/or antifungal activity. In some embodiments, the molecule or antimicrobial moiety thereof is an antibiotic. The molecule or antimicrobial moiety thereof may have a bacteriostatic or a bactericidal effect against Gram-positive bacteria, Gram-negative bacteria, or both. In some embodiments, the molecule or antimicrobial moiety thereof is effective against human or animal pathogens such as *E. coli, S. aureus* and *P. aeruginosa.*

The binding group which forms the covalent bond with the metal surface may form part of the antimicrobial moiety or it may be separate from the antimicrobial moiety. In embodiments wherein the binding group which forms the covalent bond is part of the antimicrobial moiety, it will be understood that the antimicrobial moiety is directly bound to the metal surface. In other words, there is no spacer between the metal surface and the antimicrobial moiety.

In some embodiments, some or all of the molecules consist of an antimicrobial moiety.

In some embodiments, each molecule comprises a first antimicrobial moiety and a second moiety. The second moiety may be non-antimicrobial.

It will be appreciated that the second moiety may have any desired function. For example, the second moiety may comprise one or more catalysis groups for the detection of contaminants, for example in fluid systems.

In some embodiments, the second moiety functions as a spacer between the metal surface and the first antimicrobial moiety. A spacer may advantageously allow the first antimicrobial moiety freedom of movement and reduce steric hindrance when the molecule is bound to the surface.

The spacer may have any desired size or length, for example, from 1 to 100 atoms, from 2 to 50 atoms or from 5 to 20 atoms.

In some embodiments the molecules or the antimicrobial moieties thereof are peptides. Thus, in one embodiment the invention provides a nitrided metal surface functionalized with peptides, wherein all of the peptides are immobilized on the surface by only covalent interactions between binding groups of the peptides and nitrogen sites within the metal surface. In some embodiments, the peptides are immobilized on the surface by only covalent interactions between the C-terminal carboxyl groups of the peptides and nitrogen sites within the metal surface.

In some embodiments, each peptide comprises a first antimicrobial moiety and a second moiety. The second moiety may be non-antimicrobial.

In some embodiments, the second moiety forms the C-terminus of the peptide such that the second moiety functions as a spacer between the metal surface and the first antimicrobial moiety. The spacer may be of any desired length, for example from 1 to 50, from 2 to 20 or from 5 to 10 amino acids. A spacer may advantageously allow the first moiety freedom of movement and reduce steric hindrance when the peptide is bound to the surface.

In some embodiments the molecule, peptide or antimicrobial moiety thereof comprises, or is tagged with, a detectable label. Any suitable detectable label may be used. The detectable label may be, for example, a fluorescent label or a UV-visible label. Suitable fluorescent labels include FITC and rhodamine. A convenient UV-visible label is tryptophan, which can be incorporated into a peptide chain. The more tryptophan residues present in the chain, the stronger is the reading. Other means for incorporating detectable labels will be known to those skilled in the art. A detectable label provides a convenient means by which the presence of the molecules or peptides on a surface can be detected. This can be used for quality control, for example to verify that the molecules have been successfully immobilized on the surface during the preparation process. In addition, the presence of the immobilized molecules can be checked during the life of an article comprising the surface to indicate whether the surface retains its antimicrobial activity.

In some embodiments, the molecule, peptide or antimicrobial moiety thereof has a minimum inhibitory concentration of no more than 10 mg/ml, no more than 5 mg/ml, no more than 2.5 mg/ml, no more than 1.25 mg/ml, no more than 1.0 mg/ml or no more than 0.5 mg/ml against $E.\ coli$, $S.\ aureus$ and/or $P.\ aeruginosa$.

In some embodiments, the peptide (or the antimicrobial moiety thereof) is derived from a defensin.

Defensins are small peptides expressed by epithelial and immune cells, and display antimicrobial activity against many Gram-positive and Gram-negative bacteria, fungi and viruses. The defensin may be an alpha, a beta or a gamma defensin. By "derived from" it will be understood that the peptide or antimicrobial moiety thereof may contain a part or the whole of the amino acid sequence of a defensin. Thus, in some embodiments, the peptide or antimicrobial moiety thereof comprises or consists of a defensin peptide sequence, or a functional variant or fragment thereof.

The term "variant" of a defensin peptide sequence will be understood to mean that the peptide or antimicrobial moiety thereof comprises or consists of a sequence having at least 30%, at least 40%, at least 50%, at least 60%, at least 70%, at least 80% or at least 90% identity with the amino acid sequence of a defensin peptide.

The term "fragment" will be understood to mean that the peptide or antimicrobial moiety thereof comprises or consists of a portion of a defensin peptide. The fragment may be at least 30%, at least 40%, at least 50%, at least 60%, at least 70%, at least 80% or at least 90% of the whole of the defensin peptide. The fragment may include the C-terminus or the N-terminus of the defensin peptide, or it may include neither terminus.

By "functional", it will be understood that the variant or fragment retains at least some of the antimicrobial activity of the defensin sequence from which it is derived. It will be appreciated that it may be possible to remove, add or replace one or more of the amino acids of a defensin peptide sequence to provide a variant or fragment which still displays antimicrobial activity. Indeed, a variant or fragment may have improved antimicrobial activity compared to its parent sequence. The skilled technician will know how to produce fragments and variants of known defensin sequences and test their antimicrobial properties using standard techniques. The skilled technician will also know how to calculate the percentage identity between two amino acid sequences using well-known sequence alignment tools such as ClustalW (Thompson et al., 1994, Nucleic Acids Research, 22, 4673-4680; Thompson et al., 1997, Nucleic Acids Research, 24, 4876-4882).

The peptide or antimicrobial moiety thereof may be from 5 to 40 amino acids in length. In some embodiments, the peptide (or antimicrobial moiety thereof) has at least 6, at least 8 or at least 10 amino acids (residues). In some embodiments, the peptide or antimicrobial moiety thereof has no more than 30, no more than 20, no more than 15 or no more than 12 amino acids.

Antimicrobial molecules, including peptides, are known in the art. A skilled person may employ any known antimicrobial molecule as the molecule (or antimicrobial moiety thereof) of the present invention. However, the inventors have found peptides incorporating one or more of the following characteristics to be useful.

The peptide or antimicrobial moiety thereof may comprise at least 3, at least 4 or at least 5 amino acids having a positively charged side chain. The amino acids having a positively charged side chain may be arginine (R), histidine (H), lysine (K), or any combination thereof. The positively charged amino acids may be arranged consecutively, or they may be spaced apart from each other by one or more residues. Without wishing to be bound by theory, it is thought that the association of positive charges with a bacterial cell membrane may force pore formation and induce cell death.

In some embodiments, the peptide or antimicrobial moiety thereof comprises at least 3 or at least 4 arginine residues. The arginine residues may be arranged consecutively, or they may be spaced apart from each other by one or more residues.

In some embodiments, the peptide or antimicrobial moiety thereof comprises at least one sequence of 5 or more consecutive arginine residues.

In some embodiments, the peptide or antimicrobial moiety thereof includes one or more hydrophobic and neutral amino acid residues. It is believed that the inclusion of hydrophobic and neutral residues confers broad spectrum activity. The peptide or antimicrobial moiety thereof may include from 1 to 20, from 2 to 10 or from 3 to 6 hydrophobic amino acids. By "hydrophobic and neutral amino acid" we mean alanine (A), isoleucine (I), leucine (L), methionine (M), phenylalanine (F), tryptophan (W), tyrosine (Y), glycine (G), proline (P) or valine (V).

In some embodiments, the peptide or antimicrobial moiety thereof comprises one or more hydrophilic amino acid residues. The peptide or antimicrobial moiety thereof may include from 1 to 20, from 2 to 10 or from 3 to 6 hydrophilic amino acids. By "hydrophilic amino acid" we mean serine (S), threonine (T), asparagine (N), glutamine (Q), aspartic acid (D), cysteine (C) or glutamic acid (E).

In some embodiments, the peptide or antimicrobial moiety thereof comprises at least 3 positively charged amino acids and at least one hydrophobic amino acid and, optionally, at least one hydrophilic amino acid. In some further embodiments, at least two of the positively charged amino acids are separated from each other by one or more hydrophobic and/or hydrophilic residues.

In some embodiments, the peptide or antimicrobial moiety thereof comprises or consists of a sequence having the formula $$A_{(x)}B_{(y)}A_{(x)}B_{(y)},$$

wherein:
A is a positively charged amino acid;
B is a hydrophobic amino acid or a hydrophilic amino acid;
x is a number of from 1 to 10; and
y is a number of from 1 to 10.

In some embodiments, the peptide or antimicrobial moiety thereof comprises a sequence having the formula $$A_{(x)}Z_{(w)}B_{(y)}Z_{(w)}A_{(x)}Z_{(w)}B_{(y)}Z_{(w)}A_{(x)}$$

or the formula $$A_{(x)}B_{(y)}Z_{(w)}B_{(y)}A_{(x)}B_{(y)}Z_{(w)}B_{(y)}A_{(x)}$$

wherein:
A is a positively charged amino acid;
B is a hydrophobic amino acid;
C is a hydrophilic amino acid;
x is a number of from 1 to 6;
y is a number of from 1 to 6; and
z is a number of from 1 to 6.

In some embodiments, the peptide or antimicrobial moiety thereof comprises or consists of the sequence RRYIGRGYIRR (SEQ ID No. 1).

In some embodiments, the peptide or antimicrobial moiety thereof comprises or consists of the sequence RLYLRIGRR (SEQ ID No. 2).

In some embodiments, the peptide or antimicrobial moiety thereof comprises or consists of the sequence CRVRGGRCA (SEQ ID No. 3).

In some embodiments, the peptide or antimicrobial moiety thereof comprises or consists of the sequence RRRRRR (SEQ ID No. 4).

In some embodiments, the peptide or antimicrobial moiety thereof comprises or consists of the sequence RRRRRRGALAGRRRRRRGALAG (SEQ ID No. 5).

In some embodiments, the peptide or antimicrobial moiety thereof comprises or consists of the sequence GRRRRRRGALAGRRRRRRGALAG (SEQ ID No. 6).

In some embodiments, the peptide or antimicrobial moiety thereof comprises or consists of the sequence KKKKKKGALAGKKKKKKGALAG (SEQ ID No. 7).

In some embodiments, the sequence of the peptide or antimicrobial moiety thereof comprises a terminal cysteine residue. In further embodiments, the sequence of the peptide or antimicrobial moiety thereof has a cysteine residue at each end. For example, the sequence RLYLRIGRR (SEQ ID No. 2) may be modified by the inclusion of terminal cysteine residues to give the sequence CRLYLRIGRRC (SEQ ID No. 8). In silico studies have suggested that the inclusion of cysteine residues may enable the antimicrobial moiety to reversibly cyclise through the formation of disulphide bridges, depending on the environment. Without wishing to be bound by theory, the present inventors hypothesise that the tertiary structure of the peptide or antimicrobial moiety thereof may also influence its antimicrobial activity. Combining a three-dimensional structure with positive charges in the antimicrobial moiety may help to increase the efficacy of the molecule, such as the peptide.

Thus, in some embodiments, the peptide or antimicrobial moiety thereof comprises or consists of a sequence having the formula $$C\ A_{(x)}B_{(y)}A_{(x)}B_{(y)}C,$$

wherein:
A is a positively charged amino acid;
B is a hydrophobic amino acid or a hydrophilic amino acid;
x is a number of from 1 to 10;
y is a number of from 1 to 10; and
C is a cysteine residue.

In some embodiments, the peptide or antimicrobial moiety thereof comprises or consists of the sequence CRLYLRIGRRC (SEQ ID No. 8), CRRRRRRGALAGRRRRRRGALAGC (SEQ ID No. 9), CGRRRRRRGALAGRRRRRRGALAGC (SEQ ID No. 10), CRVRGGRCAC (SEQ ID No. 11), CRRRRRRC (SEQ ID No. 12), CKKKKKKGALAGKKKKKKGALAGC (SEQ ID No. 13) or CRRYIGRGYIRRC (SEQ ID No. 14).

These sequences may be considered to be "synthetic defensins", since they are similar in structure and function to naturally occurring defensins.

As used herein, a "nitrided metal surface" will be understood as meaning a metal surface which has been treated by a process which diffuses nitrogen into the surface of the metal. The process may include nitriding, nitrocarburising (including ferretic nitrocarburising), carbonitriding and/or oxynitrocarburising (including ferretic oxynitrocarburising). These techniques will be familiar to those skilled in the art. These processes are typically used to create a case hardened surface.

In some embodiments, the depth of the nitrogen in the metal surface is at least 0.05, 0.10, 0.15, 0.20 or 0.25 mm. In some embodiments, the depth is no more than 0.30 mm. In other embodiments, the depth is no more than 0.25 mm. In another embodiment, the depth is no more than 0.20 mm. The skilled person would be aware of techniques for measuring the depth of the nitrogen.

It will be appreciated that the skilled person will be able to visually distinguish between a non-nitrided and a nitrided metal surface. A skilled person may alternatively, or in addition, employ any known technique to determine whether a surface has been nitrided. For example, a nitrided metal surface may be confirmed by testing the hardness of the metal, by using a test such as, but not limited to, the Vickers hardness test, the Knoop hardness test or the Leeb Rebound hardness test. Alternatively, or in addition, a skilled person may confirm that a metal surface is nitrided by using at least one of the techniques of EDX and X-ray diffraction, electrochemical polarization methods and electrochemical impedance spectroscopy.

The nitrided metal surface may be formed from any metal. It will be appreciated that the metal may be chosen in accordance with the intended use of the surface.

In some embodiments, the metal is iron, steel (e.g. stainless steel), titanium, aluminium, chromium, copper, silver or molybdenum, or an alloy thereof. In some particular embodiments, the metal is titanium or stainless steel. In some embodiments, the metal is copper or silver.

Since copper and silver are known to have antimicrobial properties, it may be particularly beneficial to use these metals in combination with antimicrobial molecules to provide an antimicrobial surface.

In some embodiments, the metal is steel.

The nitrided metal surface may be any surface which benefits from having antimicrobial activity. For example, the nitrided metal surface may comprise at least a portion of a surface of a worktop, a chair, a door, a handle or a railing, or any other object that comes into regular contact with humans or animals. In particular, the metal surface may comprise at least a portion of the exterior of a tool or piece of apparatus used in healthcare or food preparation. A metal surface having an antimicrobial molecule, for example, an antimicrobial peptide, immobilized thereon finds particular use in medicine, especially in medical devices.

In some embodiments, the nitrided metal surface is biocompatible. By "biocompatible", it will be understood that the metal surface is capable of existing within a human or animal body without having toxic or other deleterious effects on the human or animal. It is particularly preferred that the metal surface does not elicit an immune response. Suitable biocompatible materials include titanium or alloys thereof, stainless steel, and aluminium or alloys thereof.

The nitrided metal surface may be functionalized with a single type of molecule. In other words, all of the molecules immobilized on the surface may be identical. Alternatively, the surface may be functionalized with two or more different molecules. In some embodiments, the surface is functionalized with two or more different molecules having differing antimicrobial moieties. For example, it may be advantageous to functionalize the surface with two or more different molecules comprising or consisting of antimicrobial moieties which are effective against different microorganisms.

The nitrided metal surface may be functionalized with a single type of peptide. In other words, all of the peptides immobilized on the surface may be identical. Alternatively, the surface may be functionalized with two or more different peptides. In some embodiments, the surface is functionalized with two or more different antimicrobial peptides having differing antimicrobial moieties. For example, it may be advantageous to functionalize the surface with two or more different peptides comprising or consisting of antimicrobial moieties which are effective against different microorganisms.

The nitrided metal surface may be partially functionalized with molecules, i.e. only a portion of the metal surface may be functionalized. Thus, in some embodiments, at least 40%, at least 50%, at least 60%, at least 70%, at least 80% or at least 90% of the metal surface has molecules immobilized thereon. In some embodiments, substantially the whole of the metal surface has molecules immobilized thereon.

The nitrided metal surface may be partially functionalized with peptides, i.e. only a portion of the metal surface may be functionalized. Thus, in some embodiments, at least 40%, at least 50%, at least 60%, at least 70%, at least 80% or at least 90% of the metal surface has peptides immobilized thereon. In some embodiments, substantially the whole of the metal surface has peptides immobilized thereon.

The molecule percentage surface coverage of the metal may be determined by the use of fluorescent molecules and microscopy.

The peptide percentage surface coverage of the metal may be determined by the use of fluorescent peptides and microscopy.

The density of molecules on the metal surface may be at least 50, at least 60, at least 70, at least 80 or at least 90 micromolar per $cm^2$ of surface.

The density of peptides on the metal surface may be at least 50, at least 60, at least 70, at least 80 or at least 90 micromolar per $cm^2$ of surface.

The skilled person may employ any number of combinations of molecules on the surface, all of which are bound by covalent attachments (e.g. amide bonds) between their binding group and the nitrogen within the metal surface.

In some embodiments, there is provided a surface functionalized with at least one, at least two, at least three or at least five molecules, wherein each molecule differs from another. In some embodiments each molecule differs from another by chemical structure. In some embodiments each molecule differs from another by spectrum of activity. In some embodiments each molecule differs from another by mechanism of action. In some embodiments each molecule differs from another by class. The skilled person will be aware of the different classes of antimicrobials.

In some embodiments, there is provided a surface functionalized with at least one, at least two, at least three or at least five peptides, wherein each peptide differs from another by at least one amino acid.

The peptides may be formed by solid-phase peptide synthesis (SPPS). Further details with regards to SPPS will be known to those skilled in the art and can be found in common textbooks (e.g. Stryer, Biochemistry, W.H. Freeman and Co Ltd, 2002).

The functionalized metal surface may be long-lasting. By long lasting, it will be understood that at least 50%, at least 60%, at least 70%, at least 80%, at least 90% or at least 95% of the molecules or the peptides may be immobilized on the surface for at least 1 week, at least 2, at least 3, at least 4, at least 5, at least 10 or at least 15 weeks.

The functionalized metal surface may be hard-wearing. In some embodiments the molecules or the peptides remain immobilized on the surface after mechanical and/or chemical treatment. The mechanical treatment may comprise regular contact with humans and/or animals. By "regular contact", it will be understood that the surface is contacted at least once per day, at least once per week, at least once per month, at least once per 3 months or at least once per 6 months and that each contact lasts for at least one second. The chemical treatment may comprise treatment with alcohol (for example ethanol), Dettol®, trypsin, Vaseline®, detergent or soap, or any combination thereof. The surface may be contacted with the chemical treatment at least once per day, at least once per week, at least once per month, at least once per 3 months or at least once per 6 months and that each contact lasts for at least one second.

For the avoidance of doubt, it will be understood that the metal surface is not functionalized with any molecules, including peptides, which are immobilized by electrostatic interactions.

According to a second aspect of the invention, there is provided an article comprising the metal surface of the first aspect of the invention.

The metal surface may constitute a portion of or the whole of a surface of the article. In some embodiments, the entire article is made from the metal. Alternatively, the article may comprise a core and a metal surface in accordance with the first aspect of the invention.

The article may be, or may form a part of, a worktop, a chair, a desk or table, a door, a handle or a railing (which may be found, for example, in a public building, a business premises, in a domestic dwelling, a farm or on public transport, a keypad (for example on a cash machine or a security panel), plumbing (for example taps, pipework), catering equipment (including pans, utensils, serving receptacles and the like), a device or piece of apparatus (such as apparatus or machinery used in manufacturing or agriculture) or a medical device. A nitrided metal surface functionalized with antimicrobial molecules such as peptides can advantageously be used to inhibit or reduce the growth of microorganisms on surfaces that are frequently touched, for example door handles.

The medical device may be an implant (e.g. a dental implant, a pacemaker, a cochlear implant or an orthopaedic implant), a prosthesis (e.g. a prosthetic hip or knee, or a component thereof), analytical equipment or a surgical instrument.

According to a third aspect of the present invention there is provided a method for preparing a nitrided metal surface in accordance with the first aspect of the invention, the method comprising contacting a nitrided metal surface with molecules comprising at least one binding group and an antimicrobial moiety so as to form covalent bonds between the binding groups of the molecules and the nitrogen atoms in the surface, thereby immobilising the molecules on the metal surface.

In some embodiments, the method comprises contacting the nitrided metal surface with the molecules in the presence of a catalyst. It will be appreciated that the type of catalyst must be selected in accordance with the nature of the binding group. The skilled person will be aware of suitable catalysts for coupling different binding groups to the nitrogen atoms in the metal surface. In embodiments wherein the molecule is or comprises a peptide, a suitable catalyst is a mixture of HBTU ((2-(1H-benzotriazol-1-yl)-1,1,3,3-tetramethyluronium hexafluorophosphate)), and DIEA (N,N-Diisopropylethylamine).

The nitrided metal surface may be contacted with the molecules by any suitable means. For example, the surface may be dip-coated or immersed in a solution containing the molecules and, optionally, a catalyst.

The nitrided metal surface may be contacted with the molecules for a period of time suitable to enable covalent bonds to form between the binding groups of the molecules and the nitrogen atoms in the surface such that a desired density of molecules is achieved on the surface. In some embodiments, the surface is contacted with the molecules (e.g. a dipped or immersed in a solution containing the molecules) for a period of time of from 1 to 24 hours, e.g. approximately 12 hours.

In some embodiments, the method is carried out at a temperature of from 10 to 30° C., for example at room temperature.

In some embodiments, the molecules or the antimicrobial moieties thereof comprise or consist of peptides. Thus, in some embodiments, the method comprises contacting the nitrided metal surface with peptides so as to form covalent bonds between binding groups of the peptides (e.g. the C-terminal carboxyl groups) and nitrogen sites within the metal surface.

In some embodiments, the method further comprises preparing a nitrided metal surface. A "nitrided metal surface" will be understood as meaning a metal surface which has been treated by a process which diffuses nitrogen into the surface of the metal. The process may include nitriding, nitrocarburising (including ferretic nitrocarburising), carbonitriding and/or oxynitrocarburising (including ferretic oxynitrocarburising). Nitriding will be understood to be a treatment process in which nitrogen is diffused into the surface of a metal; nitrocarburising will be understood to be a treatment process in which nitrogen and carbon are diffused into the surface of a metal; carbonitriding will be understood to be a treatment process in which nitrogen and carbon are diffused into the surface of a metal and oxynitrocarburising will be understood to be a treatment process in which carbon, nitrogen and oxygen are diffused into the surface of a metal. Ferretic processes will be understood to mean treatment processes on ferrous metals.

There are three main methods for nitriding a metal surface: gas nitriding, in which nitrogen-rich gas, usually ammonia, is used to donate the nitrogen; salt bath nitriding, in which the nitrogen-donating medium is a nitrogen-containing salt such as cyanide salt; and plasma nitriding, in which intense electric fields are used to generate ionized molecules of gas (usually pure nitrogen) around the metal surface to be nitrided. These methods of nitriding will be known to those skilled in the art.

Embodiments of the invention will now be described by way of example, with reference to the accompanying Figures in which.

Figure 11:
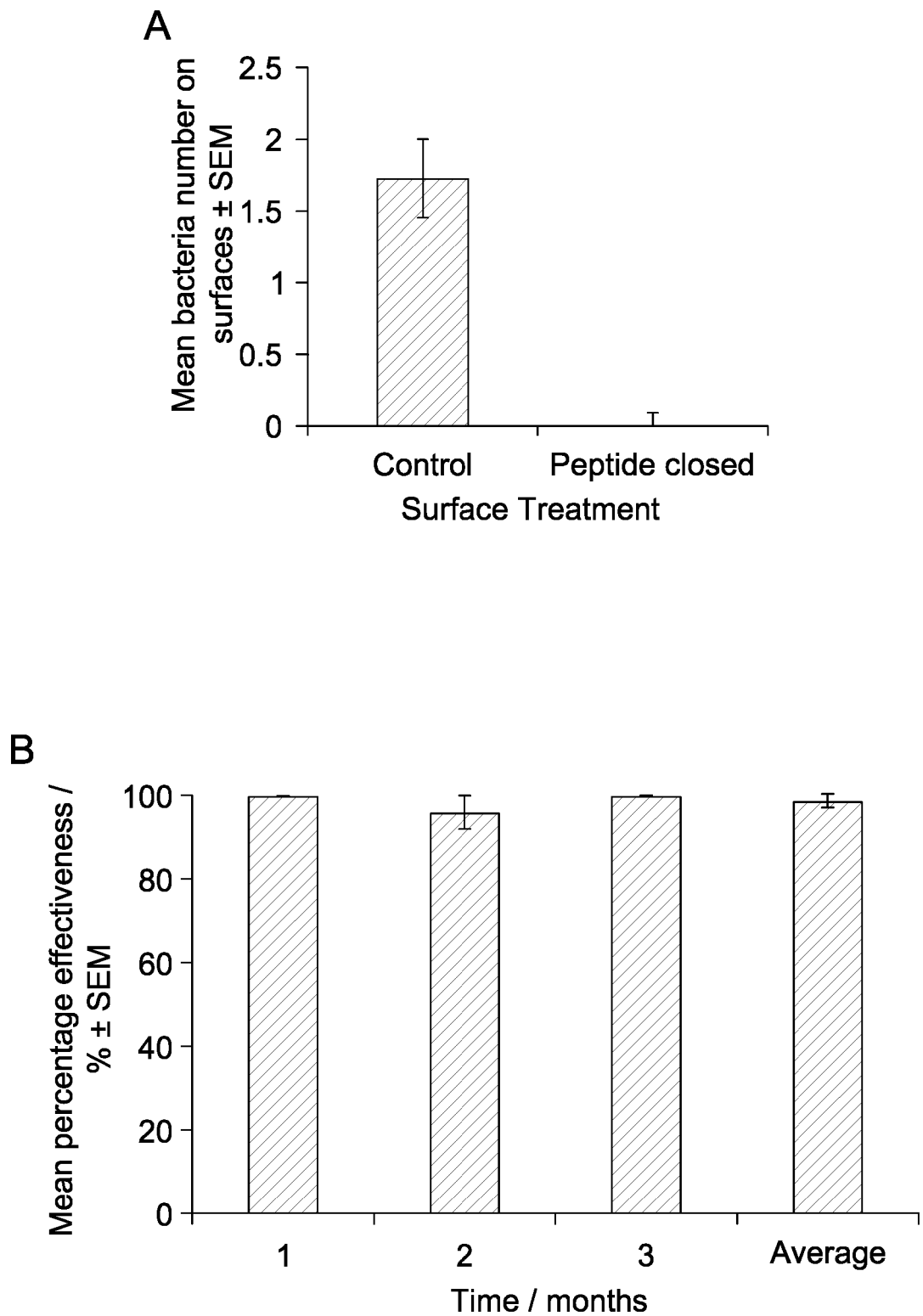
Figure 12:
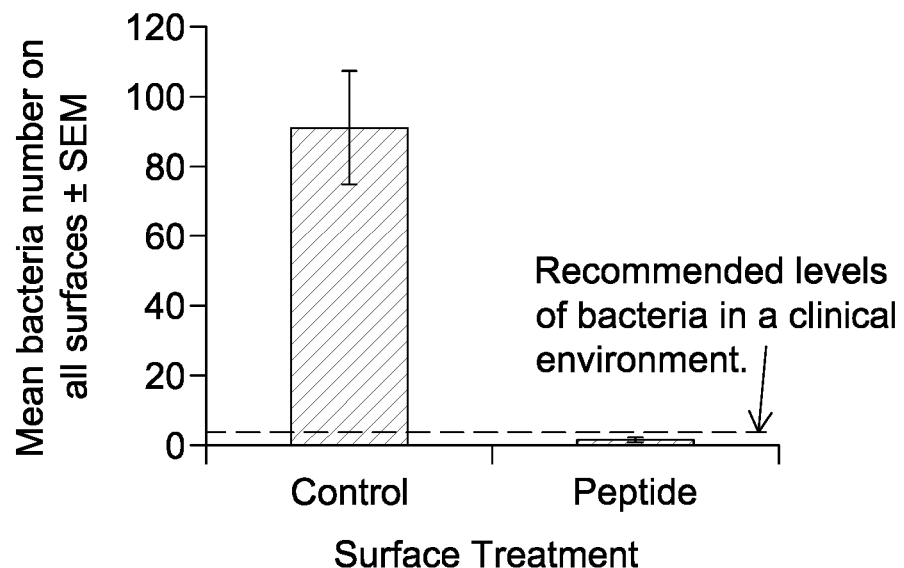
Figure 12:
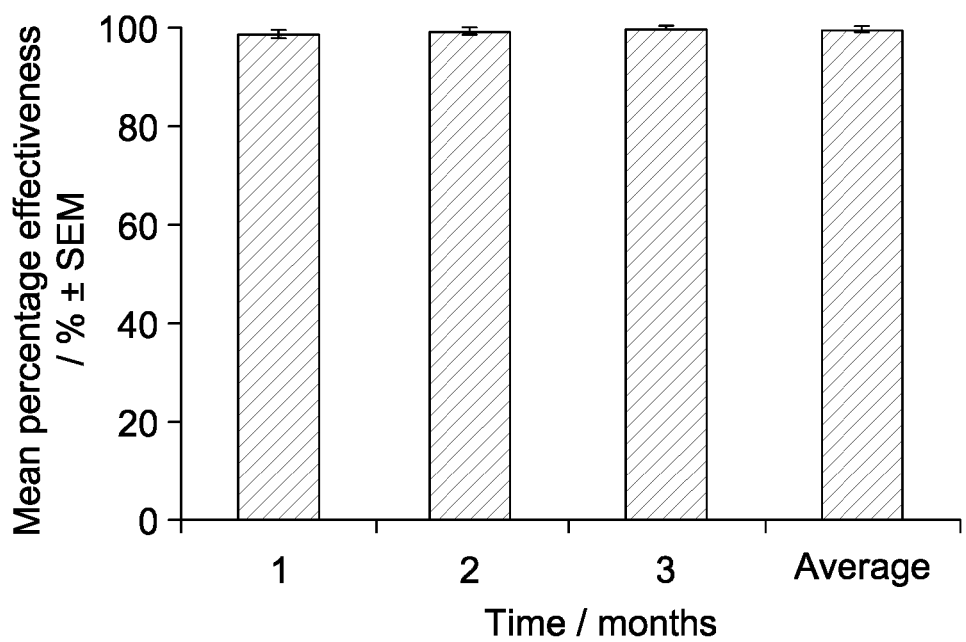
Figure 13:
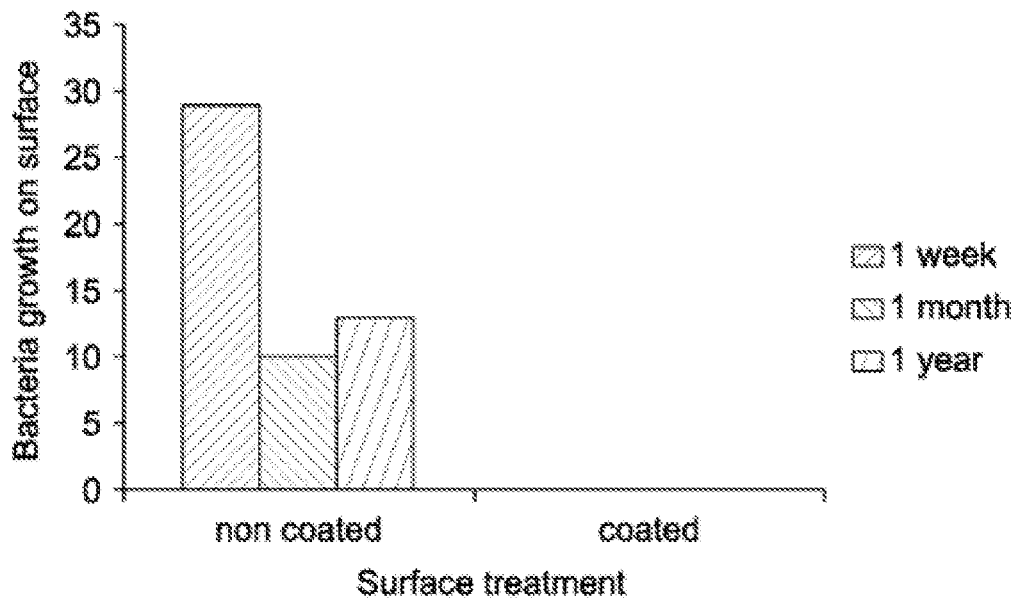
Figure 14:
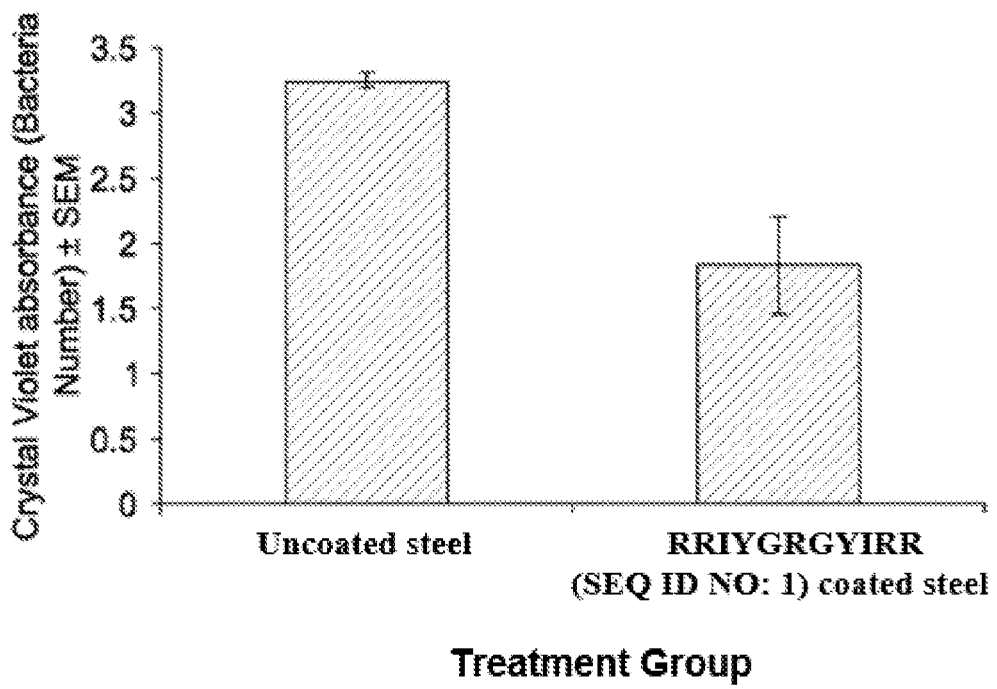

FIG. 11 shows graphs showing the anti-microbial effect of peptide-coated nitrided steel surfaces used in a hospital setting over a three-month period. (A) Absolute bacteria counts from the surfaces. Error bars show standard error of the mean. (B) Percentage effectiveness of the coated surfaces compared to control surfaces, broken down over the time of the experiment. 99% or greater efficacy was observed at all time points;

FIG. 12 shows graphs showing the anti-microbial effect of peptide-coated nitrided steel surfaces used in a city hospital setting over a three-month period. (A) Absolute bacteria counts from the surfaces. Error bars show standard error of the mean; dashed line denotes the current recommended bacterial load on hospital surfaces. (B) Percentage effectiveness of the coated surfaces compared to control surfaces, broken down over the time of the experiment. 99% or greater efficacy was observed at all time points;

FIG. 13 is a graph showing the results of a long term study of the effectiveness of peptide-coated nitrided surfaces. The data shows the bacterial growth counts on treated and non-treated surfaces in a medical school which were observed over a year; and FIG. 14 is a graph showing the absorbance of crystal violet on a peptide-coated nitrided metal surface which had been treated with bacteria. The amount of stain is directly related to the number of bacteria.

EXAMPLES

Example 1

Synthesis and Purification of Peptides

Peptides were synthesized using a standard Fmoc solid phase synthesis technique on a Liberty blue peptide synthesizer. Peptides were purified by high performance liquid chromatography (HPLC). Briefly, water and acetonitrile were added to tubes containing the solid peptides. The solutions were vortexed until the peptides had fully dissolved. Samples were filtered using a 2 μm syringe filter and analysed using a HPLC machine, which contained a C18 column. After purification, the solvents of water and acetonitrile, both with 0.05% trifluoroacetic acid, were used over a period of 40 minutes using a 0 to 100% acetonitrile gradient. This was followed by a 20 minute wash cycle consisting of 10 minutes with 100% acetonitrile, and 10 minutes with 100% water.

Preparation of Metal Surface

Nitriding of Metal

Metal surfaces were prepared using a standard plasma nitriding process by Metaltech, Consett, Co. Durham in a plasma nitride unit. Variables of the process are shown in Table 1.

TABLE 1

| Type of Steel | Incubation Temp (° C.) | Incubation Time (hours) | Depth of nitride layer (mm) |
|---|---|---|---|
| α1 | Mild | 440 | 19 | 0.15 |
| α2 | Mild | 440 | 38 | 0.25 |
| α3 | Mild | 440 | 19 | 0.1 |
| β1 | Mild | 480 | 20 | 0.05 |
| β2 | Spring | 525 | 36 | 0.25 |
| β3 | En24 | 525 | 36 | 0.25 |

Plasma Ferretic Nitrocarbursing with Post Oxidation of Metal

Metal surfaces were plasma ferretic nitrocarburised using a standard process by Metaltech. The different types of metal are shown in Table 2.

TABLE 2

| | Type of Steel | Oil blackodised? |
|---|---|---|
| P1 (PlasOx-1) | Spring | No |
| P2 (PlasOx-2) | Spring | Yes |

All pieces of steel used were cleaned with P400 grit paper and acetone.

Immobilisation of Peptide on to Nitrided Metal Surface

Nitrided metal surfaces were incubated overnight at room temperature on a rotamixer in a solution comprising a 9:0.5:0.5 ratio of dimethylformamide (DMF), DIPIA and HBTU, respectively, and 0.5 .mu.g/ml of the peptide RRRRRRGALAGRRRRRRGALAG (SEQ ID NO: 5) tagged with a fluorescent label. Following incubation, surfaces were washed with DMF, which was replenished every 5 minutes for 50 minutes, followed by saline, which was also replenished every 5 minutes for 50 minutes, before being left to air dry.

Analysis of Peptide Attachment

The peptide percentage surface coverage of the metal was assessed by the use of fluorescent peptides and microscopy. Peptide coated metal was viewed by a fluorescence microscope at an exposure of 1.55 s using a 10× objective. Nine images for each 1 cm$^2$ piece of steel were obtained. Images were analysed using ImageJ software (NIH, MD, USA). The threshold from control images, obtained from nitrided metal which had not been treated with peptide, was adjusted until all of the pixels were removed, leaving an image with no staining. This acted as a control baseline. Images from corresponding experimental samples were then adjusted to this threshold value and the residual pixel count then recorded as a measure of peptide attachment.

Results

Figure 1:
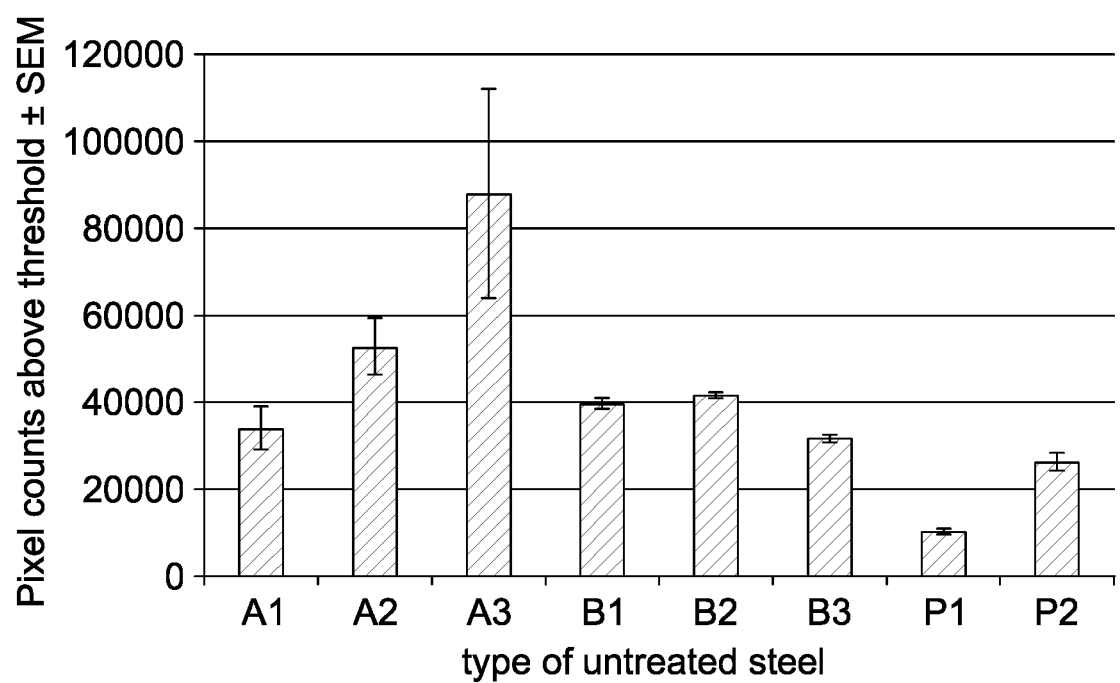
FIG. 1 is a graph showing the level of peptide fluorescence on different types of steel.

Turning to FIG. 1, it was successfully demonstrated that the peptide can be attached to the eight steel types, since all mean pixel counts were above 0. Please note that the x-axis labels A1-3 represent .alpha.1-3 steel, B1-3 represent .beta.1-3 steel and P1-P2 represent p1-p2 steel. The difference between the level of peptide attachment and steel type was significant (P=0.006, Kruskal-Wallis one-way analysis of variance with Bonferroni correction), which indicates that the peptide preferentially binds to certain steel types. It can be seen from the graph that the peptide RRRRRRGALAGRRRRRRGALAG (SEQ ID NO: 5) has the highest binding affinity for alpha steel types.

Example 2

Mild steel was nitrided using a standard process for 19 hours at 440° C. by Metaltech. The peptide RRRRRRGALAGRRRRRRGALAG tagged with a fluorescent label was immobilized on the surface of the nitrided steel as described in Example 1. Peptide-coated steel was incubated in the appropriate environmental treatment at room temperature for a suitable time which depended on the treatment used. Samples were washed with saline following treatment and peptide attachment analysed by microscopy as detailed in Example 1.

Figure 2:
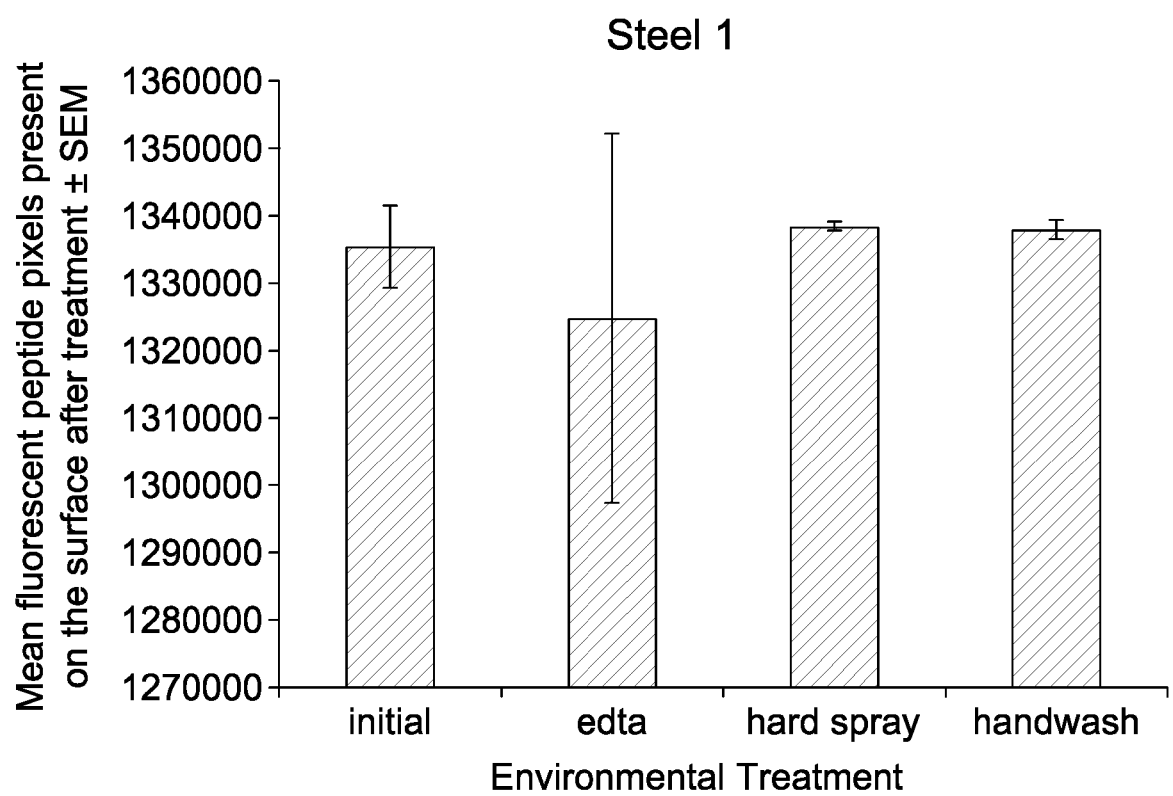
FIG. 2 is a graph showing the level of peptide fluorescence on nitrided steel following different environmental treatments.

FIG. 2 shows that the peptide coverage of the nitrided steel remains at a similar level before and after various environmental treatments.

Mild steel was nitrided using a standard process by Metaltech. The peptide RRRRRRGALAGRRRRRRGALAG (SEQ ID NO: 5) tagged with a fluorescent label was immobilized on the surface of the nitrided steel as described in Example 1. Peptide-coated steel was incubated in the appropriate environmental treatment at room temperature for a suitable time which depended on the treatment used. Samples were washed with saline following treatment and peptide attachment analysed by microscopy as detailed in Example 1.

Figure 3:
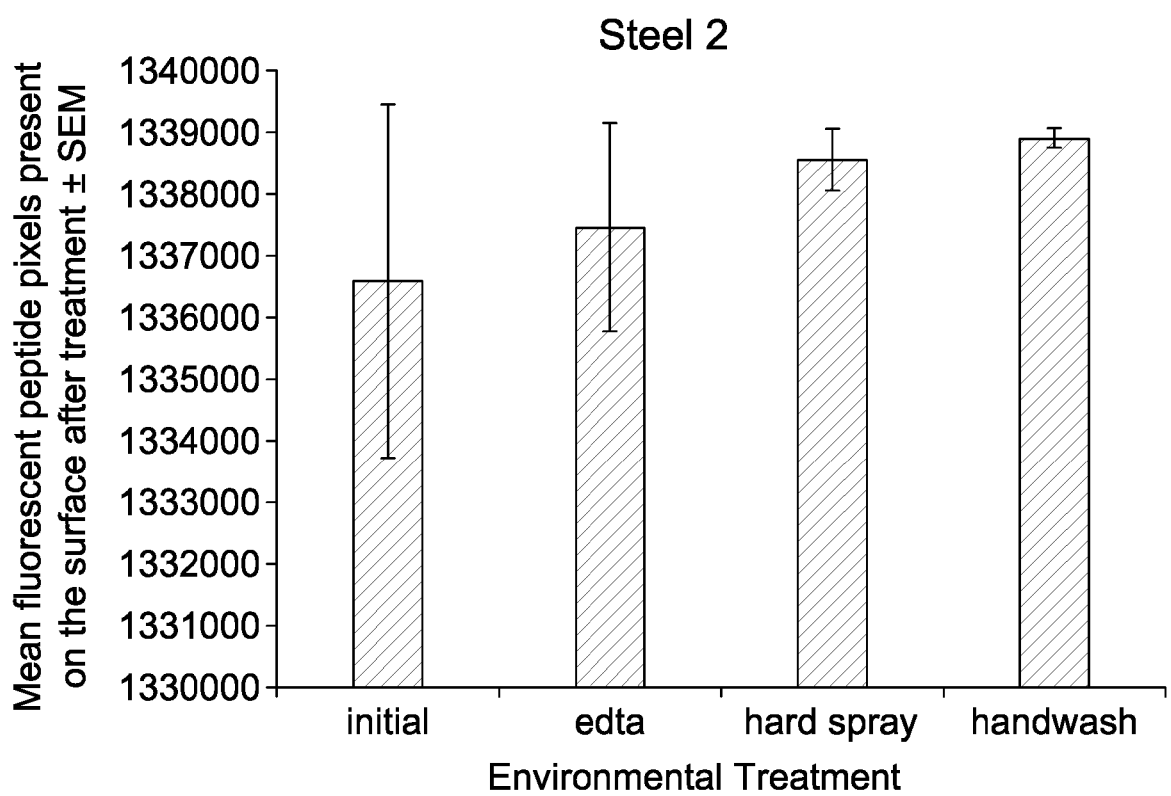
FIG. 3 is a graph showing the level of peptide fluorescence on nitrided steel following different environmental treatments.

FIG. 3 shows that the peptide coverage of the nitrided steel also remains constant following environmental treatment. This suggests that the durable and long-lasting immobilization of peptide on a nitrided surface is applicable to different steels and metals.

Example 3

Steel was nitrided or plasma ferretic nitrocarburised as described in Example 1, after which the peptide RRRRRR-GALAGRRRRRRGALAG (SEQ ID NO: 5), tagged with a fluorescent label was immobilised on the nitrided surface as described in Example 1.

Figure 4:
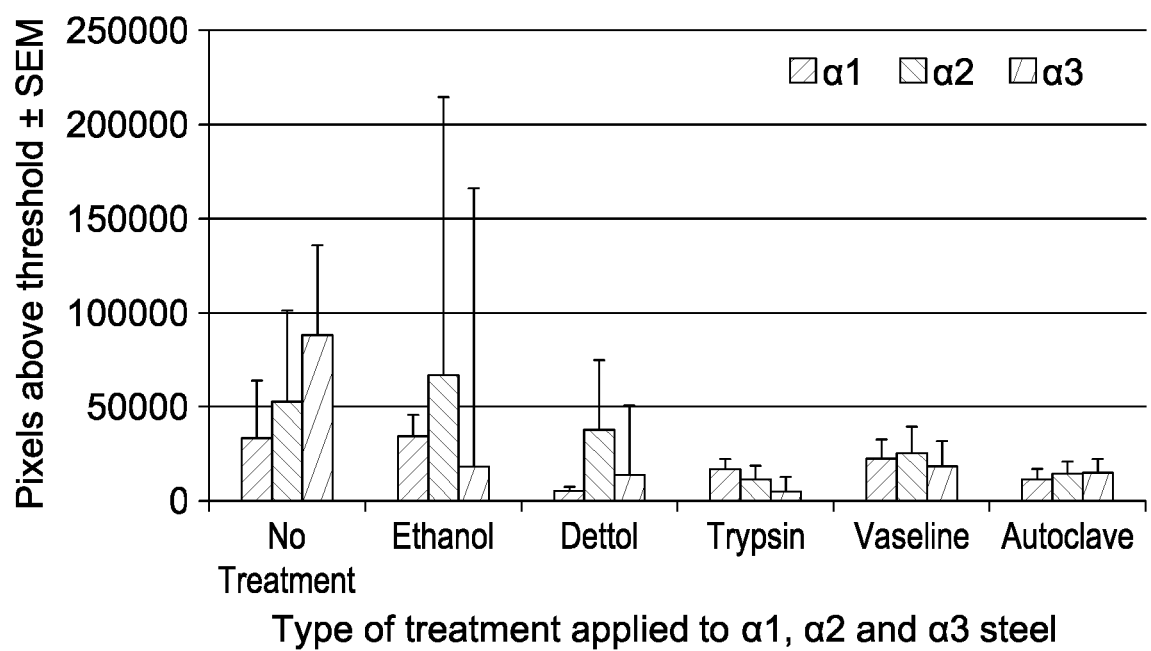
FIG. 4 is a graph showing the level of peptide fluorescence on α1-3 steel following different treatments.

Peptide-coated alpha steel samples were incubated in various standard cleaning or coating treatments at room temperature, for a suitable time which depended on the treatment used, in order to determine if any of these treatments affected the attachment of the peptide to the steel. FIG. 4 shows the pixels above threshold (indication of extent of peptide coverage) for each nitrided, peptide coated surface, following a particular treatment. A statistically significant difference was found in the pixel counts between treatments for α1 steels (H=19.4 p=0.004) and α3 steels (H=12.8, p=0.047). This decrease may be partly accounted for by loss of fluorescence over the period of 3 weeks as the steel pieces were repeatedly exposed to light. However, no significant difference was observed between pixel counts following various environmental treatments of α2 steels (H=12.4, p=0.053).

Figure 5:
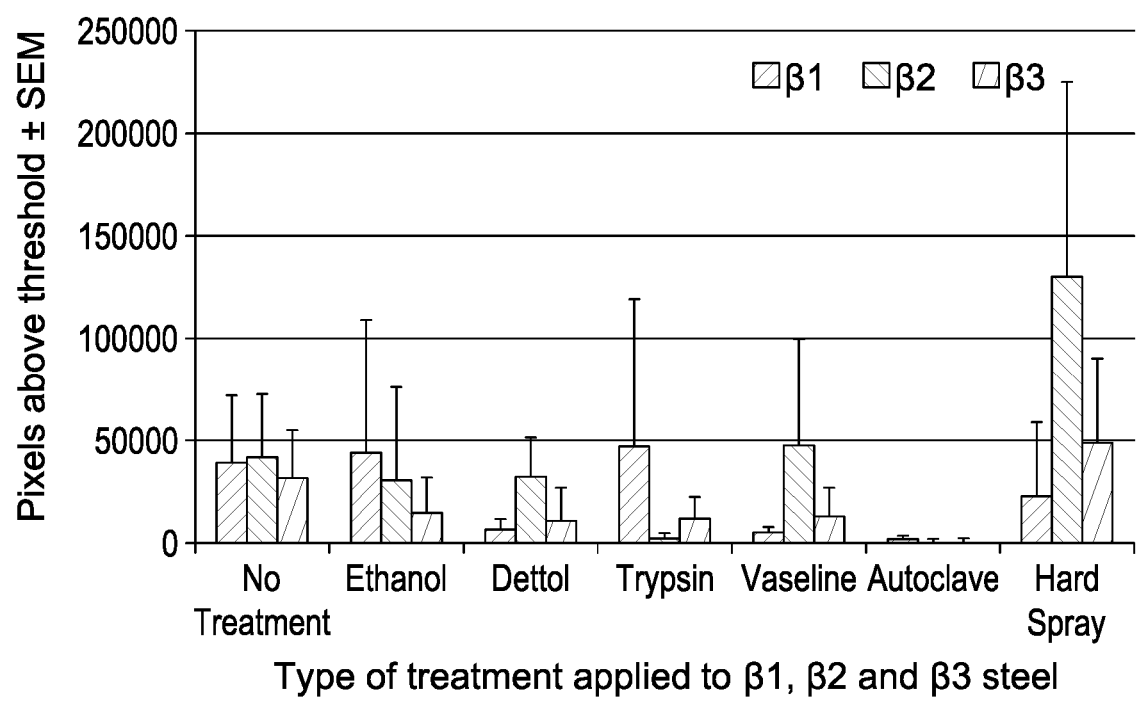
FIG. 5 is a graph showing the level of peptide fluorescence on β1-3 steel following different treatments.

FIG. 5 shows the pixels above threshold for each nitrided, peptide coated beta steel. Statistical analysis indicated that environmental treatment does not affect the peptide coverage of β1 and β steels, since no significant difference was observed between treatments (H=10.6, p=0.103) and (H=10.9, p=0.09), respectively. A significant difference was observed between different treatments for the P2 steel group (H=13.7, p=0.033).

Figure 6:
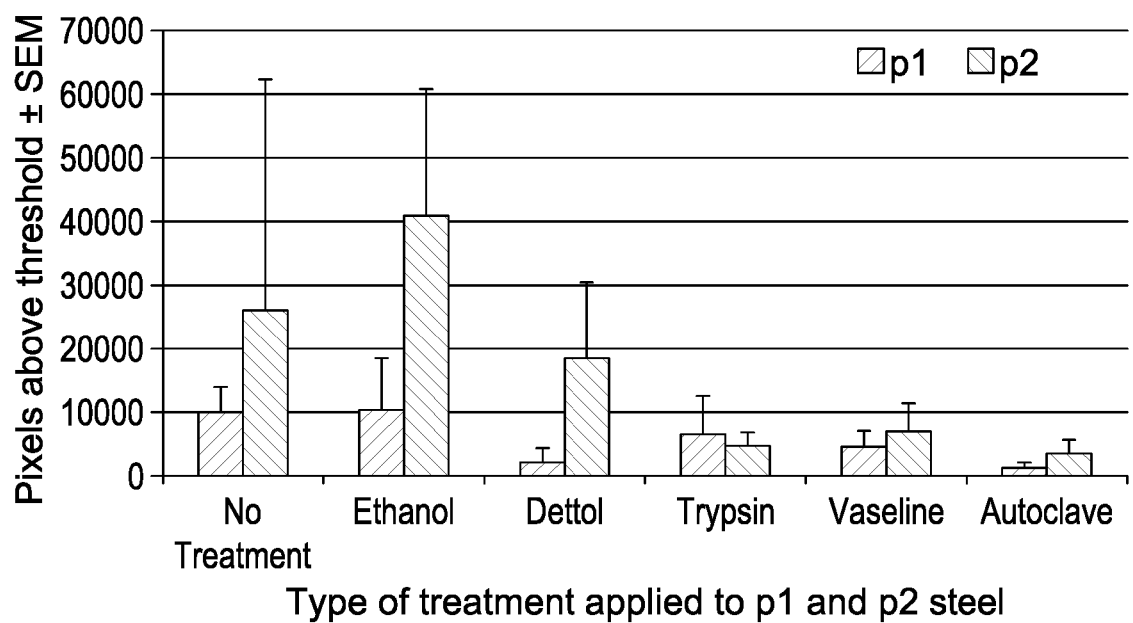
FIG. 6 is a graph showing the level of peptide fluorescence on p1 or p2 steel following different treatments.

FIG. 6 shows the pixels above threshold for peptide coated PlasOx steel, following environmental treatment. In most instances, the pixel number was found to be higher for PlasOx 2 steel than PlasOx 1 steel. Differences in pixel number between treatments were found to be significant for both metals (PlasOx 1 steel, H=15.4 p=0.017 and PlasOx 2 steel, H=12.7 p=0.048).

Example 4

.alpha.2 steel was prepared using a standard nitriding process and coated with 1 .mu.g/ml of the unlabelled peptide RRRRRRGALAGRRRRRRGALAG (SEQ ID NO: 5) using the method as described in Example 1. Peptide coated, or control uncoated steel samples were then attached to areas where high colony forming unit (CFU) counts were predicted (e.g. toilet seat, kitchen tap etc.). Cotton wool buds, dipped in saline, were used to swab surfaces on days 1, 2, 7, 8 and 9. Buds were placed in sterelin tubes and used to inoculate blood agar plates, following which plates were incubated for 48 hours at 37.degree. C. before CFU counts were taken.

Figure 7:
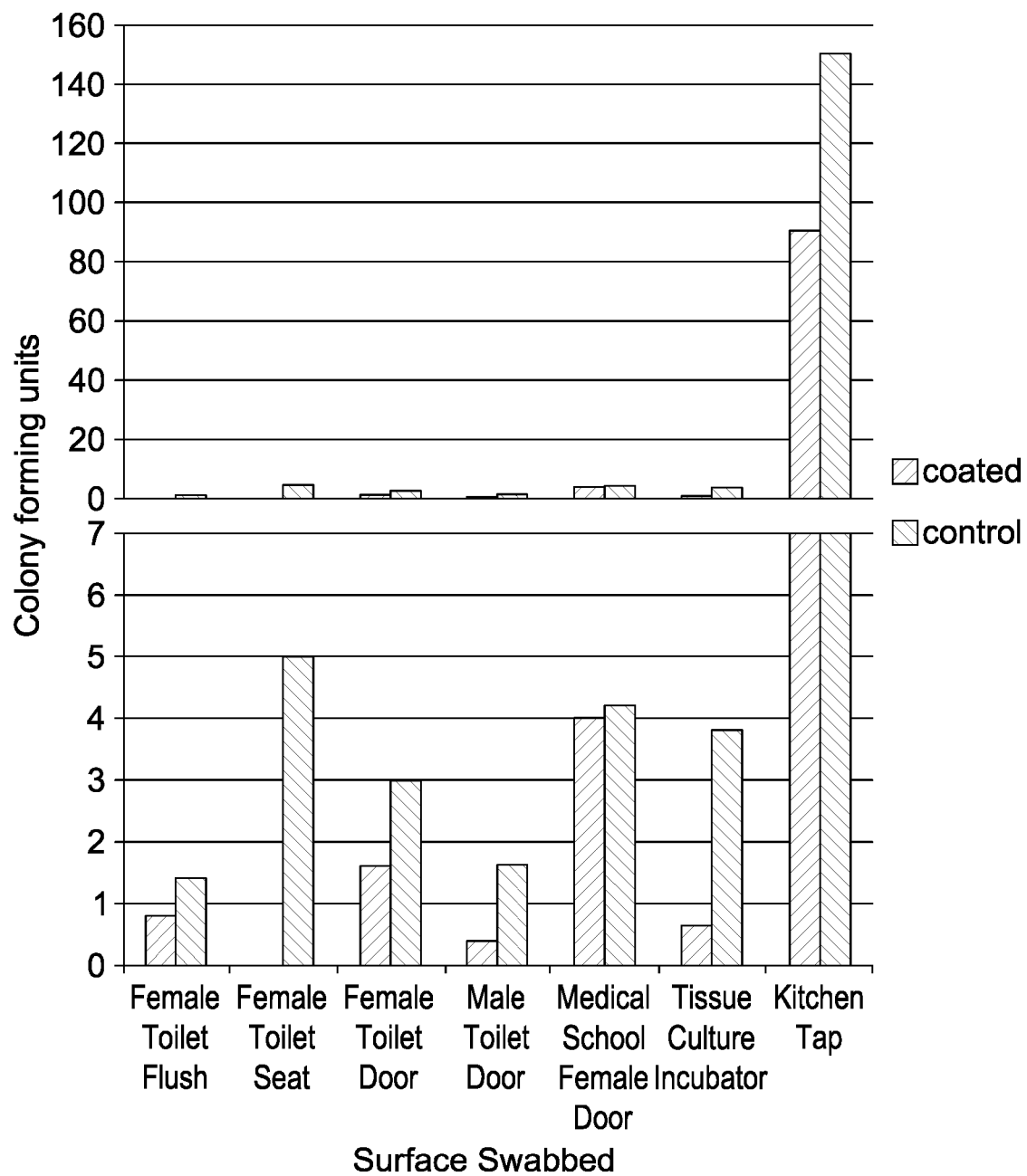
FIG. 7 is a graph showing the colony forming units taken from control and peptide coated pieces of nitrided steel placed on different surfaces.

FIG. 7 shows the mean CFU count on peptide coated versus control nitrided alpha 2 steel surfaces after attachment to a particular surface. The results demonstrated a consistently higher mean CFU count on control pieces of metal, in comparison to peptide-coated pieces of steel, from all areas tested.

Example 5

Having established the durability and the efficacy of immobilized peptides on a steel surface, the efficacy of peptides immobilized on a titanium surface was assessed. Nitrided titanium was prepared by Metaltech. RRRRRR-GALAGRRRRRRGALAG (SEQ ID NO: 5), tagged with a fluorescent label, was immobilised on the surface of the nitrided titanium as described previously. Peptide-coated samples were incubated in PBS solution at room temperature for between 1 and 4 weeks, following which fluorescence, and the resulting pixel number above threshold, was assessed as described previously by fluorescence microscopy.

Figure 8:
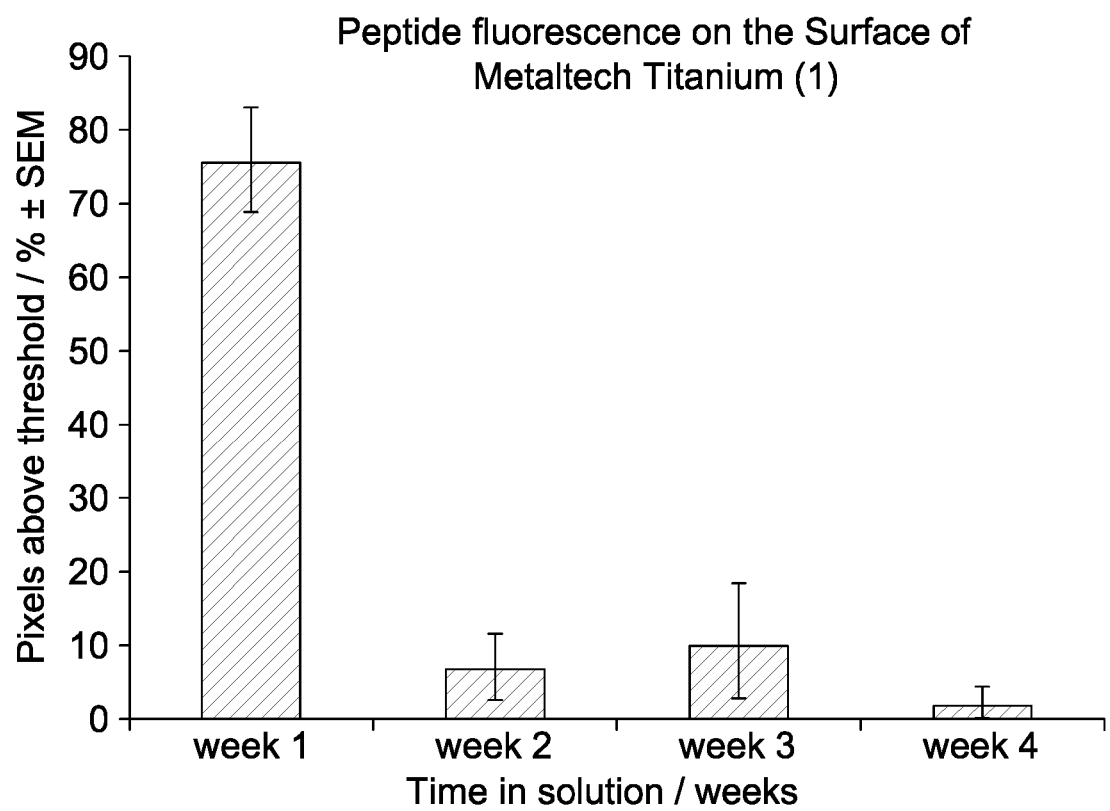
FIG. 8 is a graph showing the level of peptide fluorescence on Metaltech nitrided titanium over a period of time.

FIG. 8 shows the mean pixel number above threshold on the surface of nitrided titanium after 1, 2, 3 or 4 weeks in PBS solution. The highest mean pixel number was observed following 1 week in solution. Although pixel number decreased considerably between 1 and 2 weeks, after 2 weeks pixel number remained relatively constant. Pixels were observed above the threshold after 1, 2, 3 and 4 weeks in solution, indicating that the interaction between the peptide and the nitrided titanium surface is long-lasting.

Example 6

Figure 9:
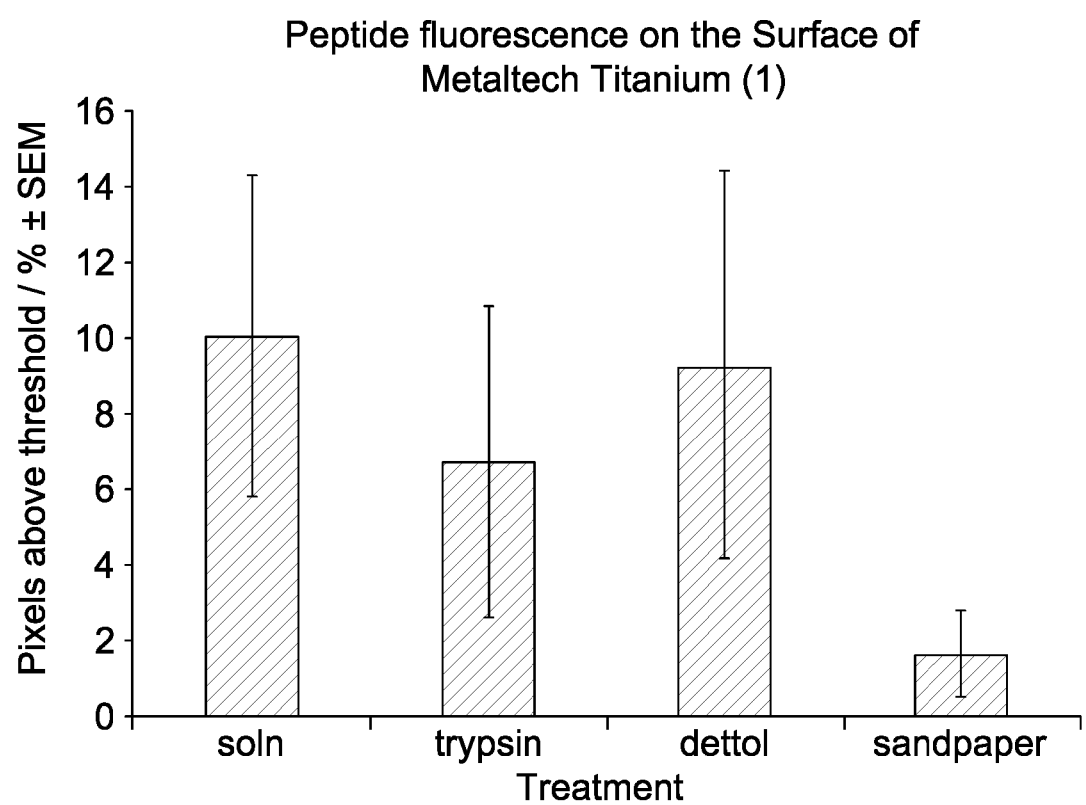
FIG. 9 is a graph showing the level of peptide fluorescence on Metaltech nitrided titanium following different treatments.

The durability of immobilized peptide on the surface of nitrided titanium was assessed following different environmental treatments, as shown in FIG. 9. RRRRRRGALAGR-RRRRRGALAG (SEQ ID NO: 5)-coated titanium was incubated in control PBS solution, trypsin, Dettola or treated with sandpaper at room temperature for a suitable time which depended on the treatment used. The mean pixel number above the threshold was then assessed by fluorescence microscopy. Importantly, peptide fluorescence was retained after any of the environmental treatments, indicating a strong and durable interaction between peptide and metal. Peptide fluorescence remained similar whether treated with control solution, trypsin or Dettol®. Moreover, peptide fluorescence was retained, albeit at a lower level, following mechanical agitation using sandpaper, suggesting that the covalent interaction between peptide and surface can withstand mechanical or chemical treatment.

Example 7

Figure 10:
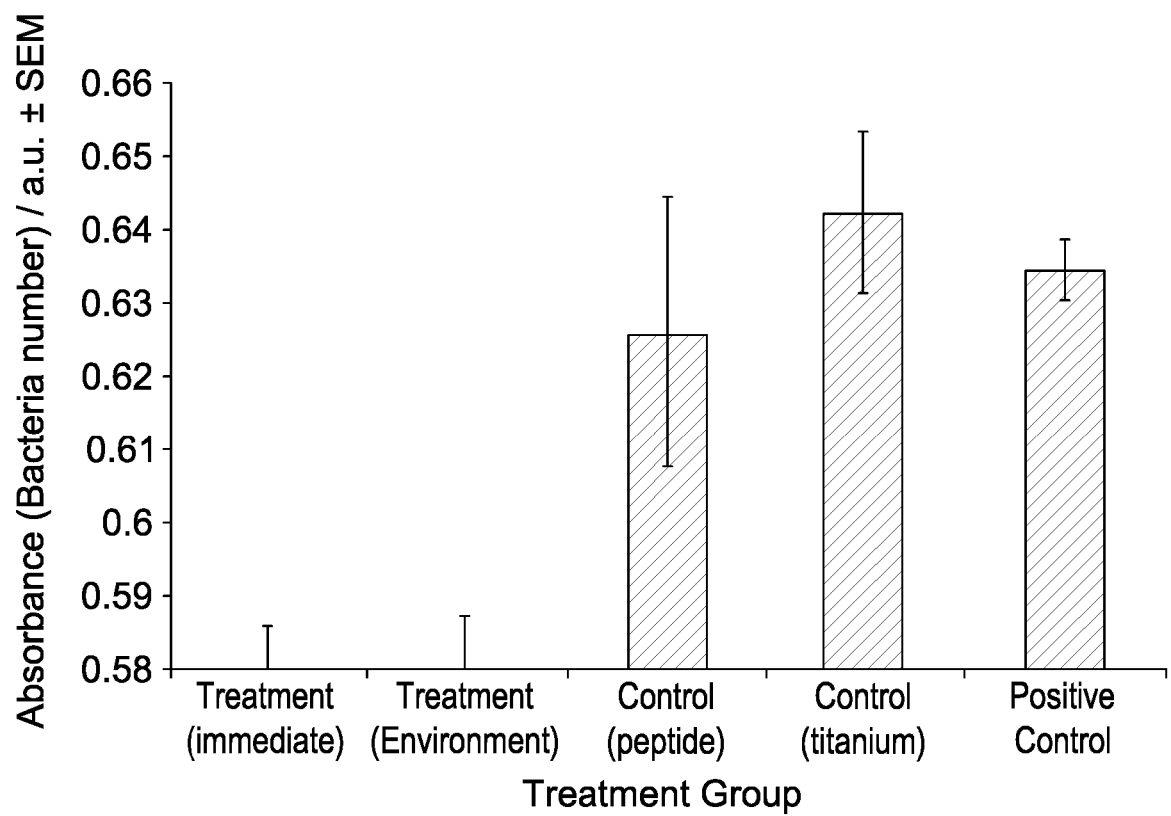
FIG. 10 is a graph showing peptide activity on the surface of Metaltech nitrided titanium.

Nitrided titanium was prepared by Metaltech, and coated as described previously with the peptide RRRRRRGA-LAGRRRRRRGALAG (SEQ ID NO: 5), aside from a control (peptide) group in which nitrided titanium was coated with a non-antimicrobial peptide, and a control (titanium) group where the nitrided titanium remained uncoated. A positive control group, consisting of uncoated tissue culture plastic, was also used. The surfaces were washed and used as growth plates for bacteria. One group of antimicrobial peptide-coated titanium surfaces was immediately used as a growth plate for bacteria (treatment (immediate)). Another antimicrobial peptide-coated titanium group (treatment (environment)) was treated with PBS, followed by trypsin/EDTA, followed by Dettol followed by sandpapering, following which the surfaces were used as a growth plate for bacteria. The Absorbance relates to the bacteria number growing on the surface after incubation (FIG. 10). Low values indicate no bacterial growth, while high values indicate high numbers of bacteria. FIG. 10 shows very low absorbance values for antimicrobial-peptide-coated titanium, in comparison to the controls where high absorbance values were observed.

Example 8

A nitrided steel surface was coated with the peptide RRRRRRGALAGRRRRRRGALAG (SEQ ID NO: 5). The surface was dip-coated in a mixture of the peptide (3 .mu.l of 10 mg/ml peptide per cm.sup.2 of metal) and a catalyst (HBTU/DIEA mix) which adhered the peptide to the surface. Coating was carried out at room temperature for 12 hours.

Coated and uncoated steel surfaces were installed in a hospital unit, in the Accident and Emergency room, Operating Theatre, Ward 1 and the associated bathroom. Control surfaces and coated surfaces were situated in identical locations and tested over three months. After use the samples and data collected were sent to the University of Birmingham for analysis.

The data obtained is presented in FIG. 11. The coated surfaces showed complete inhibition of bacterial growth. No colony forming units (cfu) were seen on any surface which had been coated with the peptide except one plate. This showed one cfu in month 2. It is believed this was due to contamination during the swabbing or plating process. Control plates showed growth of both bacteria and fungus.

The coating did not reduce the wear resistance of the surfaces, promote rust or induce any other operational problem.

Example 9

A further study was carried out in the Outpatients area of a city hospital. This is a very busy area of the hospital and sees a high volume of patient and staff traffic. The peptide used was RRRRRRGALAGRRRRRRGALAG (SEQ ID NO: 5), and the coated steel surfaces were prepared as in Example 8.

Control and coated surfaces were placed on door handles in the Outpatients area. Control surfaces demonstrated that the bacteria levels in the hospital were significantly higher than the recommended standard for hospital surfaces (5 cfu). Interestingly, only bacterial growth was seen, not fungus. The peptide-coated surfaces significantly reduced levels of bacteria down to 1 cfu with a greater than 99% effectiveness observed (FIG. 12). We saw 1 colony growth from the surfaces, which is believed to be due to the frequency of use of the surfaces. Surfaces were touched on average every 2 minutes during an observation period and, in a lot of cases, the surfaces had been touched immediately prior to the swabbing being undertaken. The fact that such a significant decrease was observed demonstrates that the surfaces are efficacious and capable of preventing colonization of the surface by bacteria but that the surface may take longer than 30 seconds to kill the bacterial cell.

Example 10

The peptide-coated surfaces described in Examples 8 and 9 were installed in a medical school. The surfaces were placed on taps in the toilets and were swabbed over a period of one year. The data (FIG. 13) shows that after 12 months inhibition of bacterial growth was still observed on the treated surfaces.

Examples 8-10 demonstrate that a nitrided metal surface functionalized with an antimicrobial peptide can inhibit bacterial growth and maintain the same level of efficacy over extended periods of time in a clinical environment.

Example 11

Nitrided steel was incubated with a solution of an antimicrobial peptide having the sequence RRIYGRGYIRR (SEQ ID NO: 1) (25 .mu.l, 10 mg/ml/cm.sup.2) at room temperature for 1 hour with a HBTU/DIEA catalyst in DMF to produce a coated surface.

Coated surfaces were inoculated with $1 \times 10^9$ bacterial cells (S. epidemridis) and incubated overnight at 37° C. The surfaces were then washed with PBS and stained using Crystal Violet (a nuclear stain) for 15 minutes at room temperature. The surfaces were washed three times to remove any residual stain and the stain lifted in 70% ethanol. The absorbance of crystal violet was read at 560 nm to quantify the level of stain (FIG. 14). The amount of stain is directly related to the number of bacteria. This demonstrates the peptide coating on the surface can significantly reduce the number of bacteria adhering to the surface.

The present invention thus provides a functionalized surface, in particular a metal surface having molecules, including peptides, immobilized thereon by only covalent interactions. The present inventor has found that the use of covalent interactions to immobilize peptides on a nitrided metal surface is an effective antimicrobial mechanism, by reducing microbial number and remaining functional for a prolonged period of time. Moreover, it has been demonstrated that the peptide-coated surface is effective against microbes even in areas exposed to high CFUs, indicating that this is an efficient mechanism for areas difficult to clean, those that are not cleaned regularly, or those that are exposed to high numbers of pathogens.

The invention claimed is:

1. A nitrided metal surface functionalized with molecules, each molecule comprising at least one binding group and an antimicrobial moiety, wherein all of the molecules are immobilized on the surface by only covalent interactions between the binding groups of the molecules and nitrogen atoms within the nitrided metal surface.

2. A nitrided metal surface according to claim 1, wherein the binding group is a carboxyl group.

3. A nitrided metal surface according to claim 1, wherein each molecule further comprises a second moiety.

4. A nitrided metal surface according to claim 3, wherein the second moiety functions as a spacer between the metal surface and the antimicrobial moiety.

5. A nitrided metal surface according to claim 1, wherein the antimicrobial moiety is antibacterial.

6. A nitrided metal surface according to claim 1, wherein the molecule or the antimicrobial moiety thereof is a peptide.

7. A nitrided metal surface according to claim 6, wherein the peptide or the antimicrobial moiety thereof is derived from a defensin.

8. A nitrided metal surface according to claim 6, wherein the peptide or the antimicrobial moiety thereof comprises or consists of a defensin peptide sequence, or a fragment or variant thereof.

9. A nitrided metal surface according to claim 6, wherein the peptide has at least 6 amino acids.

10. A nitrided metal surface according to claim 6, wherein the peptide comprises at least 3 amino acids selected from arginine (R), histidine (H), lysine (K) or any combination thereof.

11. A nitrided metal surface according to claim 6, wherein the peptide comprises or consists of any one of the following sequences:

RRYIGRGYIRR, (SEQ ID NO: 1)

RLYLRIGRR, (SEQ ID NO: 2)

CRVRGGRCA, (SEQ ID NO: 3)

RRRRRR, (SEQ ID NO: 4)

RRRRRRGALAGRRRRRRGALAG, (SEQ ID NO: 5)

GRRRRRRGALAGRRRRRRGALAG, or (SEQ ID NO: 7)

KKKKKKGALAGKKKKKKGALAG. (SEQ ID NO: 9)

12. A nitrided metal surface according to claim 1, wherein the metal is iron, steel, titanium, aluminium, chromium or molybdenum, or an alloy thereof.

13. A nitrided metal surface according to claim 1, wherein the surface is functionalized with two or more different molecules having differing antimicrobial moieties.

14. An article comprising the nitrided metal surface according to claim 1.

15. The article according to claim 14, wherein the nitrided metal surface constitutes a portion of or the whole of a surface of the article.

16. The article according to claim 14, wherein the article is or forms a part of a worktop, a chair, a desk or table, a door, a handle, a railing, a keypad or a medical device.

17. A method for preparing a nitrided metal surface comprising nitrogen atoms functionalized with molecules, the method comprising contacting a nitrided metal surface with molecules, each molecule comprising at least one binding group and an antimicrobial moiety, so as to form covalent bonds only between the binding groups of the molecules and the nitrogen atoms in the nitrided metal surface, thereby immobilizing the molecules on the metal surface.

* * * * *